United States Patent [19]

Brooks, Jr. et al.

[11] Patent Number: 4,714,474
[45] Date of Patent: Dec. 22, 1987

[54] TIBIAL KNEE JOINT PROSTHESIS WITH REMOVABLE ARTICULATING SURFACE INSERT

[75] Inventors: John G. Brooks, Jr., Memphis; Walter P. Spires, Jr., Cordova, both of Tenn.

[73] Assignee: Dow Corning Wright Corporation, Arlington, Tenn.

[21] Appl. No.: 861,892

[22] Filed: May 12, 1986

[51] Int. Cl.$^4$ .............................................. A61F 2/38
[52] U.S. Cl. .................................................... 623/20
[58] Field of Search ................................... 623/16–23

[56] References Cited

U.S. PATENT DOCUMENTS

| | | | |
|---|---|---|---|
| 4,016,606 | 4/1977 | Murray et al. | 623/20 |
| 4,207,627 | 6/1980 | Cloutier | 623/20 |
| 4,257,129 | 3/1981 | Volz | 623/20 |

FOREIGN PATENT DOCUMENTS

| | | | |
|---|---|---|---|
| 3433264 | 3/1986 | Fed. Rep. of Germany | 623/20 |
| 2129306 | 5/1984 | United Kingdom | 623/20 |

OTHER PUBLICATIONS

Brochure, "Whiteside Ortholoc(TM) Total Knee System", Dow Corning Wright Corp., Arlington, TN, No. L095-0101, 12 pp., 1983.
Brochure, "New Jersey Tricompartmental Total Knee System with Porocoat(®), Surgical Procedure", DePuy, Inc., Warsaw, IN, No. 7.5 M1084 0601-71 (Rev. 1), 22 pp., 1984.
Brochure, "The Miller/Galante Porous Tivanium(®) Total Knee", Zimmer, Inc., Warsaw, IN, No. 84-038-5780-0352/15 MA, 18 pp., 1984.
Brochure, "Choice. The Miller/Galante Total Knee System, " Zimmer, Inc., Warsaw, IN, No. 86-038-57-80-0509/16MA, 18 pp., 1986.
Brochure, "Zimmer Intramedullary Knee Instrumentation for the Miller/Galante Total Knee System", Zimmer, Inc., Warsaw, IN, No. 86-038-5780-0525/16MA, 32 pp., 1986.
Brochure, "The Intermedics Natural-Knee(TM) System", Intermedics Orthopedics, Austin, TX, No. 2/86/7.5M, 16 pp., 1986.
Brochure, "Orthomet", Orthomet, Inc., Minneapolis, MN, 2 pp., 1986.
Sketch of "OMKnee by Orthomet, Inc." by John G. Brooks, Jr., received Mar. 4, 1986, 1 p.

*Primary Examiner*—Richard J. Apley
*Assistant Examiner*—David J. Isabella
*Attorney, Agent, or Firm*—Richard E. Rakoczy

[57] ABSTRACT

This invention provides an improved implantable tibial component comprising an implantable tibial base containing two separate, opposed raised walls which engage oppositely configured recesses in the lower surface of a removable hard polymeric condylar articulating surface insert. The locking mechanism which holds the insert within the base provides a means by which the insert can be locked within the base in a secure fashion. The locking mechanism further provides a means by which the insert can be removed from the implanted tibial base in a simple fashion by raising the anterior end of the insert over the top of the anterior wall on the edge of the tibial base and sliding the insert anteriorly out of the posterior raised walls which also extend along the medial and lateral edges of the tibial base.

5 Claims, 19 Drawing Figures

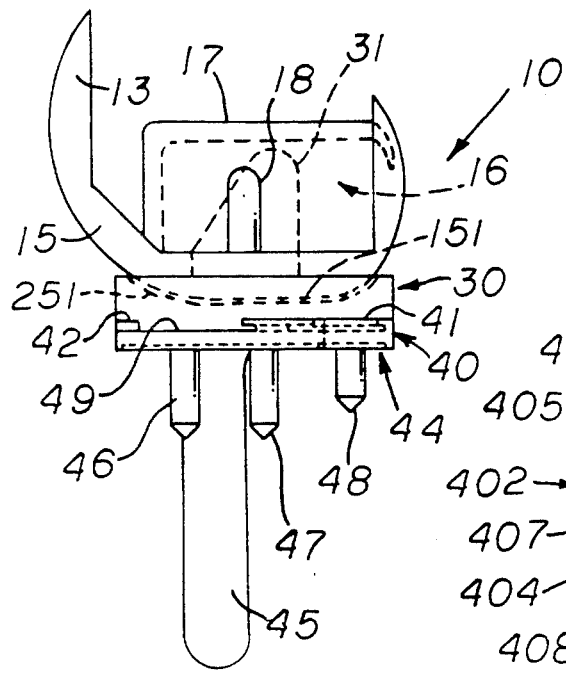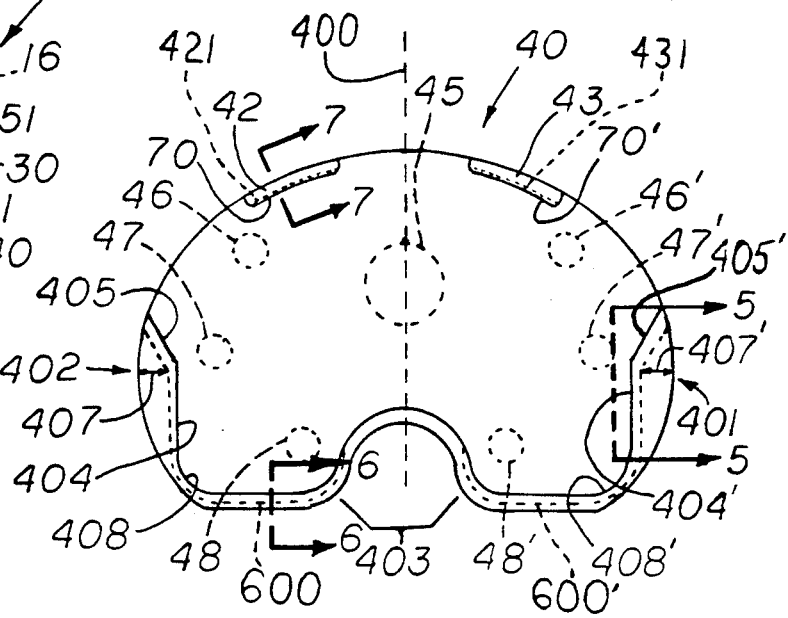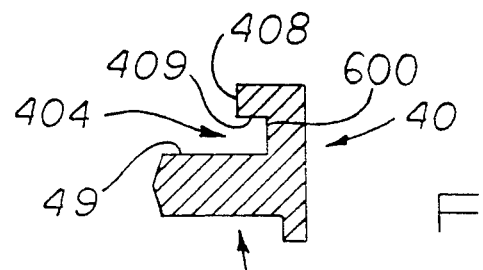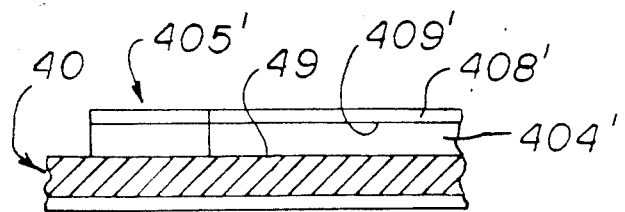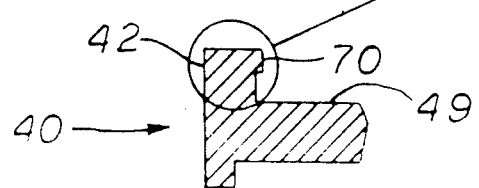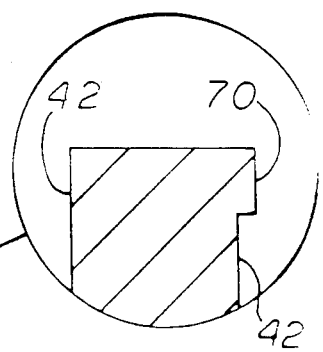

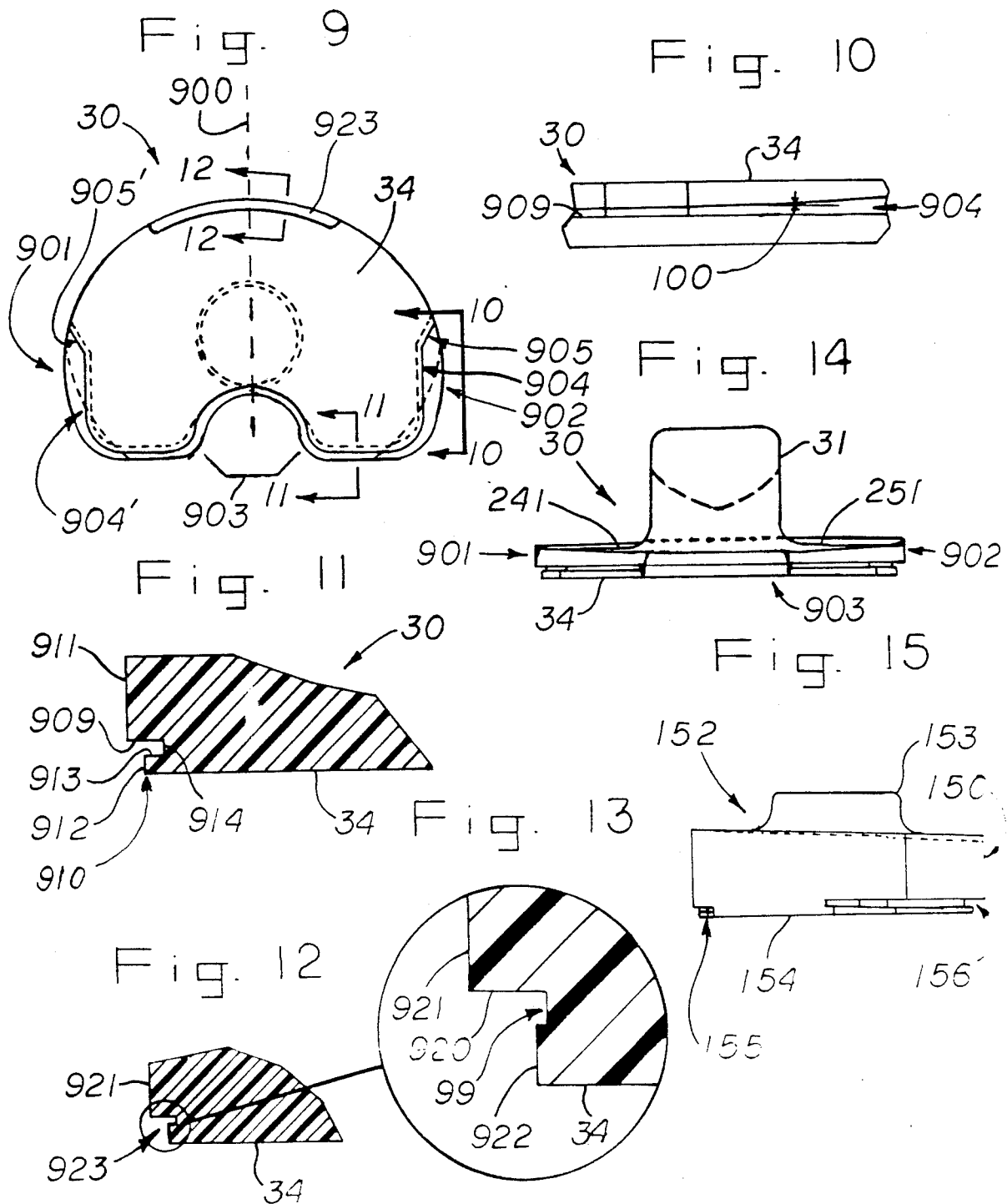

TIBIAL KNEE JOINT PROSTHESIS WITH REMOVABLE ARTICULATING SURFACE INSERT

BACKGROUND OF THE INVENTION

This invention relates to surgically implantable knee joint prostheses and more particularly to improvements in tibial components of such devices.

Knee arthroplasty is becoming more common to partially or totally replace knee joints which have been damaged due to trauma or disease. In some cases, only one compartment of the knee joint need be replaced while in other cases, both compartments of the femoral and tibial articulating surfaces must be replaced. Based upon the condition of the ligaments and tendons surrounding the joint, the surgeon selects a knee joint prosthesis which provides the necessary degree of stability to the joint. Implantation of such prostheses involves accurately shaping the ends of the bones to receive each component of the prosthesis in proper alignment and thereafter insuring that each component is properly sized to permit the repaired joint to function normally as best as is possible.

Prosthesis manufacturers provide a range of trial components to assist the surgeon in selecting appropriately sized components. For the tibial components, the surgeon is provided with a trial tibial base which is placed on the prepared tibial plateau and, for example, a set of slide-in plastic trial tibial base inserts (containing an articulating surface for femoral condyles) in various sizes which correspond to permanently implantable tibial prostheses. The trial base is notched to receive the oppositely notched underside of the trial inserts so that the surgeon can slide in a trial insert and test the joint for proper flexion, etc. The process may be repeated a number of times until a trial insert is found which is properly sized for the patient's knee joint. The trial base and trial insert are then removed and a permanent implant corresponding to the size of the trial tibial insert/base combination is then fixed to the tibial plateau. See, for example, Dow Corning Wright Corporation (Arlington, Tenn.) Brochure No. L095-0101 (12 pp., 1983) entitled "Whiteside ORTHOLOC (TM) Total Knee System" which shows one such trial base and trial insert design. The inserts freely slide in and out of the tibial base.

Other removable tibial base insert prostheses have been taught and used in the past, some to eliminate the need for a separate trial base. U.S. Pat. No. 4,016,606 to Murray, et al. (issued 4/12/1977) teaches a planar tibial base insert which is affixed within an implantable tibial base by sliding the tapered notched lower part of the insert into a tapered oppositely notched area in the tibial base and then locking the insert into the tibial base by means of a pin passing through the metal base and the insert. This has the disadvantage of requiring a separate pin to lock the insert in place although the patent does suggest that one might be able to omit the locking pin. Another example of slide-in tibial insert (one for each condyle) is shown as a "meniscal bearing" in DePuy, Inc (Warsaw Ind.) Brochure No. 7.5 M1084 0601-71 (Rev. 1) entitled "New Jersey Tricompartmental Total Knee System With POROCOAT (®), Surgical Procedure" (22 pp., 1984).

U.S. Pat. No. 4,207,627 to Cloutier (issued 6/17/1980) teaches the use of drop-in tibial inserts, one for each condyle. Each insert is placed in a recess in the implantable tibial base and the front of each insert is grooved to mate with an oppositely-grooved portion of the tibial base. The back portion of the insert is not grooved and simply butts against the wall of the recess. The back portion of the insert is therefore not locked in place. The removable inserts enable a surgeon "to obviate any misalignment, natural or not," although in doing so, the surgeon would have to remove the insert laterally where several ligaments are located rather than anteriorly.

In U.S. Pat. No. 4,257,129 (issued 3/24/1981), Volz teaches a replaceable articulation member tibial component which employs a central vertical pin and a two-prong horizontal clip which locks the articulation member in place after it is slid onto the tibial base up to a raised stop means. One object is to provide an articulation member which can easily be replaced in the event that the articulating surface of the removable member becomes worn. Use of a pin and a clip adds additional complexity to the manufacture and insertion/removal of the member. The Volz patent also suggests a tibial base and removable articulation member having raised dovetail bosses to retain the insert within the base, but does not tell how—other than by a "snug sliding fit" or interference fit—that removable member is to be locked into place to prevent it from sliding in the direction opposite (anteriorly) the raised tab in the base used to stop the member upon insertion.

A more recent removable tibial base insert prosthesis which can be removed anteriorly from the tibial base and which locks in place without a need for the clips and/or pins noted above is described in Zimmer, Inc. (Warsaw, Ind.) Brochure No. 84-038-5780-0352/15MA entitled "The MILLER/GALANTE Porous TIVANIUM (®) Total Knee" (18 pp., 1984). The tibial base is permanently implantable while various sized tibial articulating surface inserts can be fixed and removed using an inserting and a removing instrument. The tibial insert is slid over and secured to a central, approximately dove-tailed, eminence on the tibial base and the outside periphery of the base drops within a raised peripheral rim on the tibial base. Because the only point of actual attachment to the tibial base is at the central eminence, the tibial insert may become stressed and possibly lift away from the tibial base at one side or another in response to lateral movement of the knee joint since there is no locking attachment to the sides of the tibial base. While the Miller/Galante knee is not offered with posterior stabilized knee components, if such were available, this stressing and lifting of the tibial insert becomes more probable. If a posterior-stabilized knee prosthesis with a raised central post on the tibial insert is used with this type of removable tibial insert design, the post is designed to provide stability to the knee by fitting within and being constrained by an intercondylar recess in the femoral component of the total knee prosthesis. Lateral movement of the knee may cause the post to press against the walls of the recess and result in stress and possible lifting of the insert from the tibial base. In addition to stressing the tibial insert, when a posterior-stabilized knee prosthesis is used, the knee joint itself might possibly feel somewhat loose if the insert should bend and lift when subjected to a lateral motion since a great deal of force is exerted on the knee joint during articulation.

SUMMARY OF THE INVENTION

One object of the present invention is to provide a permanently implantable tibial prosthesis component with a removable tibial base insert which can accommodate a variety of tibial base insert thicknesses and designs. The tibial prosthesis component can replace the articulating surfaces of one or both proximal tibial articular surfaces.

Another object of the present invention is to further overcome the disadvantages of prior art removable tibial base insert prostheses by providing a tibial component having a removable insert which locks within an implantable tibial base to provide lateral and medial stability to the insert as well as resistance against anterior and posterior movement of the insert. This object is accomplished in a simple manner without a need for additional locking pins and the like to hold the tibial insert against the tibial base.

These and other objects of the present invention are provided by a surgically implantable knee joint prosthesis for the replacement of one or both articulating surfaces of a proximal tibia comprising an implantable base of, for example, a surgically implantable metal such as cobalt- or titanium-base metal alloys having a lower surface which is adapted to be permanently affixed to a surgically prepared superior tibial surface and an upper surface having a first retaining wall means comprising at least one undercut raised retaining wall extending along at least a portion of the peripheral edge of the posterior region of the upper surface of the base and further extending along at least a portion of the peripheral medial and lateral edges of the upper surface of the base and a second raised retaining wall means on the upper surface which is opposite and separated from the first wall means on both the lateral and medial edges of the base, the second wall means comprising at least one raised wall extending along at least a portion of the central one-fourth to two-thirds of the peripheral edge of the anterior region of the upper surface, and a removable articulation insert of a hard synthetic polymer such as ultrahigh molecular weight. polyethylene having an upper surface which is configured to receive at least one condyle present on a distal femur situated above the tibia and a lower surface which is adapted to closely mate with and slidingly engage the first wall means and to pass over and contact the second wall means in a locking engagement such that the insert is firmly held within the base until such time as the insert is released by raising the lower surface of the insert above the second wall and sliding the insert anteriorly away from the implantable base. Preferably, the second wall means also contains a recess which the anterior surface of the insert engages to provide a stronger locking engagement.

BRIEF DESCRIPTION OF THE DRAWINGS

The invention will become better understood by those skilled in the art from a consideration of the following description when read in connection with the accompanying Drawings wherein:

FIG. 2 is a side view showing the manner (in partial shadow) in which the femoral component cooperates with the tibial component of the present invention.

FIG. 4 is a top view of the tibial base.

FIGS. 5-8 are partial cross-sectional views of the tibial base of FIG. 4 detailing the manner in which the raised walls are constructed.

FIG. 9 is a bottom view of the removable articulation insert of the present invention.

FIGS. 10-13 are partial cross-sectional views of the removable articulation insert of FIG. 9 detailing the portions of the insert which receive the raised walls of the tibial base.

FIG. 14 is a rear (posterior) view of the removable articulation insert of FIG. 9.

FIG. 15 is a side view of an alternative embodiment of a removable articulation insert.

DETAILED DESCRIPTION OF THE INVENTION

Figure 1:
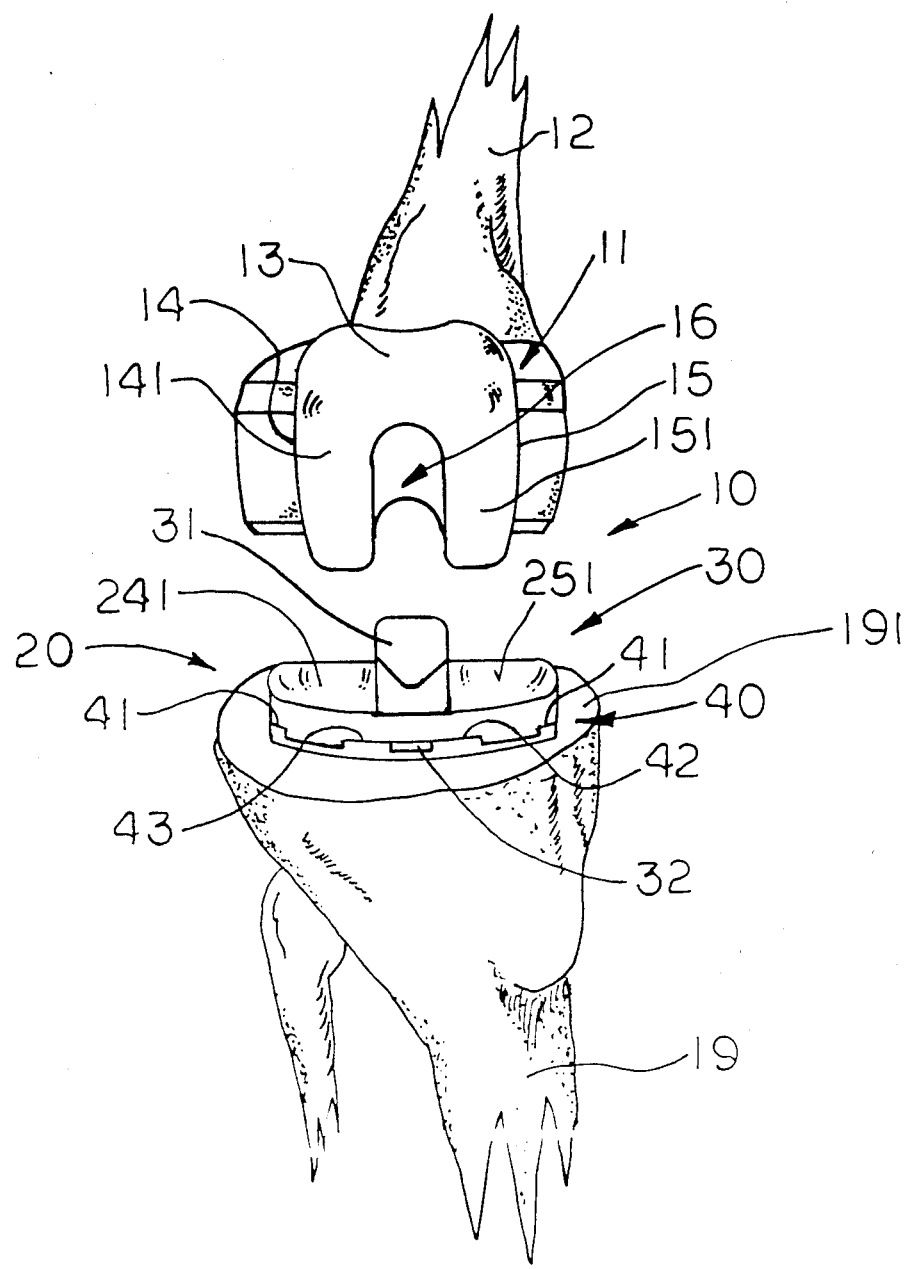
FIG. 1 is a perspective view of the tibial prosthesis of the present invention implanted within a knee joint along with a femoral component.

Referring to the Drawings, FIG. 1 depicts a front (anterior) view and FIG. 2 shows a side (medial) view of a posterior-stabilized knee prosthesis 10 as it would appear within the right knee after implantation with most of the associated anatomical structures removed for purposes of clarity. FIG. 1 shows the knee in flexion. For purposes of definition, terms commonly used in defining directions with respect to the knee joint shall also be applied to the prostheses and components thereof being described. Thus, "anterior" means the "front" and "posterior" means the "rear" or "back" while "medial" means "toward the center of the body" or on the "left side" for the right knee joint and "lateral" means "away from the body" or on the "right side" for the right knee joint. The following will describe the invention in terms of a prosthesis for the right knee, but it is understood that the invention can also be used for a left knee prosthesis.

Prosthesis 10 is composed of metal femoral component 11 of conventional design which has been fixed to the distal surface of femur 12. Component 11 is composed of patellar flange 13 having spaced apart lateral condyle 14 and medial condyle 15 extending down from flange 13 with an intercondylar recess 16 located between condyles 14 and 15. As can be seen in FIG. 2, recess 16 is formed by intercondylar stabilizing housing 17. Peg 18 on condyle 15 and a similar peg located in the same place on condyle 14 assist in securing component 11 to femur 12.

Tibial component 20 is shown affixed to the superior surface 191 of proximal tibia 19 and is composed of articulation insert 30 which is shown as being locked within permanently implantable tibial base 40. The upper surface of insert 30 contains a central stabilizing post 31 which is closely received within recess 16 to provide stability to the knee joint after implantation of prosthesis 10. The upper surface of insert 30 also contains two concave surfaces 241 and 251 which act as articulating surfaces for the lower curved surfaces 141 and 151, respectively, of condyles 14 and 15. As shown in FIG. 2 for medial condyle 15, surface 251 closely approximates the contour of surface 151 and the same is true for surface 241 with respect to surface 141. This configuration permits prosthesis 10 to restore articulation to the knee joint.

The lower portion of insert 30 is configured to be received within tibial base 40 in a locking engagement in a manner that will be more fully described with respect to FIGS. 9–14. Posterior raised wall 41 which extends across the entire posterior peripheral edge of tibial base 40 and along a portion of the medial and lateral peripheral edge of tibial base 40 and anterior raised walls 42 and 43 serve to securely lock insert 30 onto the upper surface 49 of base 40. The space 32 between walls 42 and 43 provides a place where a tool can be inserted to assist a surgeon in lifting the lower surface of insert 30 up and over walls 42 and 43 to permit removal of insert 30 from base 40.

The lower surface of base 40 contains an optional indented area 44 shown in relief which may optionally be filled with sintered porous beads or with wire mesh to promote bone ingrowth and improve fixation of the tibial base 40 to tibia 19. Central peg 45 along with pegs 46, 47 and 48 (there are also corresponding pegs 46', 47' and 48' opposite these) serve to mechanically hold the tibial base 40 on tibia 19.

Both components of prosthesis 10 are fixed to the surfaces of femur 12 and tibia 19 according to procedures which are well known to those skilled in the art and which form no part of the present invention.

Figure 3:
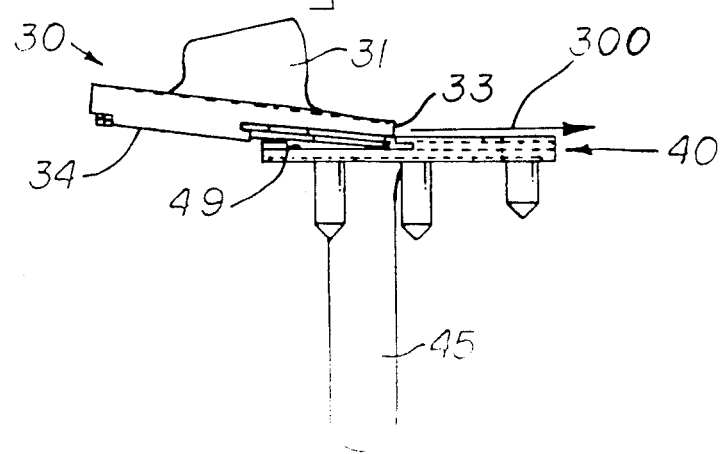
FIG. 3 is a side elevational view showing the insertion of an articulation insert into a tibial base.

FIG. 3 depicts the simple method by which insert 30 is locked within base 40. The lower surface of the posterior edge 33 of insert 30 is engaged within the medial and lateral edges of raised wall 41 and is pushed posteriorly in the direction of arrow 300. The flat lower surface 34 of insert 30 contacts the upper surfaces of walls 42 and 43 until the posterior edge of insert 30 reaches the posterior edge of base 40. At that time, anterior recess 923 in insert 30 is now even with walls 42 and 43 and surface 34 drops towards and rests on flat upper surface 49 of base 40. Walls 41, 42 and 43 now engage insert 30 within base 40 in a locking, secure fashion as shown in FIGS. 1 and 2. To remove insert 30, a prying tool is inserted within space 32 and the lower edge of insert 30 is raised above walls 42 and 43, and then the procedure described above for insertion is reversed. Alternatively, an inserter or removal tool which grips a notch in the metal edge of base 40 and exerts an upward and posterior (insertion) or anterior (removal) force against insert 30 such as the tools described and sold in connection with the above-described MILLER/GALANTE Porous TIVANIUM Total Knee tibial component can be adapted for use with tibial component 20.

Referring to FIGS. 4–8, the specifics of the preferred manner in which the implantable tibial base of the present invention is constructed will now be given. Tibial base 40 is preferably constructed of a surgically implantable grade of metal such as a cobalt- or titanium-base alloy of the type commonly employed for surgically implantable prostheses; the exact nature of the material forms no part of the present invention provided that it is strong enough to retain the insert 30 within base 40 under conditions expected during use.

The posterior wall means comprises posterior wall 41 which contains an undercut 404' along the lateral edge 401 and a corresponding undercut 404 along the medial edge 402 of base 40 and each undercut 404 and 404' continues symmetrically on each side until area 403 of wall 41 is reached. To guide insert 30 into base 40, areas 405 and 405' are tapered and the undercut runs parallel to each edge until the posterior edge of base 40 is reached. Area 403 of wall 41 is solid and, along with the remaining posterior edges of wall 41, serves to force wall 922 of anterior recess 923 of insert 30 against surface 421 of wall 42 and the corresponding surface 431 of wall 43 to insure that a locking engagement is obtained.

FIG. 5 shows a partial cross-section of the lateral edge 401 of base 40 showing undercut 404' with tab 408'. The lower surface 409' of tab 408' runs parallel to upper surface 49 of base 40. Surface 49 is preferably substantially flat and planar. FIG. 6 shows the detail of the posterior portion of wall 41 in cross-section further showing interior surface 600 of wall 41 against which surface 912 of insert 30 ultimately rests. Interior surface 600' provides a surface against which the corresponding surface of insert 30 opposite surface 912 rests.

An anterior wall means comprising at least one raised wall running along the anterior edge of base 40 is necessary to retain insert 30 within base 40 in locking engagement. Without such a wall, insert 30 would tend to move anteriorly and slip away from the base when the knee is flexed. This wall preferably runs along the central one-fourth to two-thirds of the anterior peripheral edge of base 40 and is preferably symmetrically located with respect to a line dividing the medial half of base 40 from the lateral half. The drawings show a more preferred embodiment wherein the wall means is two anterior walls 42 and 43 where the central space between walls 42 and 43 is employed to provide a means for lifting the anterior edge of insert 30 over walls 42 and 43. There must be a sufficient amount of separation between the medial edges of walls 41 and 42 and likewise between the lateral edges of walls 41 and 43 to permit the insert 30 to engage wall 41 and slide into base 40; otherwise the insert could not be used.

FIG. 7 shows a cross-sectional view of wall 42; wall 43 has the same configuration. FIG. 8 is an enlarged view of the circled portion of FIG. 7 showing the details of the preferred embodiment where walls 42 and 43 each contain a lip 70 and 70', respectively, which extends toward the center of base 40.

Base 40 as well as insert 30 can be manufactured by conventional techniques such as by casting and machining the material selected into the shapes described above.

Hard polymeric articulation insert 30 will now be described with reference to FIGS. 9–14. FIG. 9 shows insert 30 viewed from below and shows in shadow the manner in which insert 30 contains undercut 904' near the lateral edge 901 of insert 30 and undercut 904 near medial edge 902 of insert 30. Each undercut 904 and 904' begins at tapered area 905 and 905', respectively, and continues symmetrically on each side as until each undercut ends at the beginning of area 903. Area 903 has no undercut and the plastic in that area is removed so that the solid raised wall area 403 of base 40 fits tightly within area 903. It should be obvious that the undercut and cutout areas on preferably substantially flat and planar surface 34 of insert 30 correspond to the opposite features associated with the upper surface 49 of base 40.

FIG. 10 is a side view of a portion of medial edge 902 showing the manner in which undercut 904 is tapered at an angle shown at reference numeral 100 so as to lead undercut wall 41 within the opposite undercut 904 when insert 30 is inserted within base 40.

FIG. 11 shows a cross-sectional view of the posterior edge of insert 30 showing how the shape of the undercut is opposite that for corresponding undercut 404 in base 40. Tab 910 is simply omitted in area 903. Undercut 904' on lateral edge 901 has the same configuration as undercut 904.

FIG. 12 shows a cross-sectional view of anterior recess 923 which receives walls 42 and 43 in base 40. FIG. 13 is an enlarged view of the circled portion of FIG. 12 showing the details of the preferred embodiment where recess 923 contains a second recess 99 which receives lips 70 and 70' of base 40 to result in a tighter locking engagement.

Insert 30 can be made of any biocompatible hard synthetic polymeric material which is suitable for implantation within the human body and has physical properties which permit the above-described sliding and locking engagement as well as sufficient resistance to wear to permit its use as an articulating surface for a knee prosthesis. One material which is preferred is ultrahigh molecular weight polyethylene of the type which is commercially available and commonly used for tibial prosthesis articulating surfaces. Another example of a hard polymeric synthetic material which may be useful is carbon fiber-reinforced polyethylene.

It was also found that ultrahigh molecular weight polyethylene had another property which suited it for use in the present invention: the expansion coefficient of the plastic resulted in a significant change in dimensions upon going from room temperature to body temperature. This property enables one to manufacture an articulation insert which is slightly smaller in size (i.e., up to 0.012 in. or 0.305 cm) than is required to obtain a tight fitting, but still removable insert. Upon warming to body temperature, the plastic insert expands and improves the locking engagement of the insert within the tibial base. After an insert is selected and inserted, a greater degree of locking engagement is obtained once the insert warms to body temperature.

FIG. 14 shows a rear view of insert 30 which is designed for use with a posterior-stabilized knee prosthesis. FIG. 15 shows an alternative insert 150 which is similar to insert 30 and locks within base 40. Insert 150 has upper articulation surface 152, central post 153, and substantially flat lower surface 154 with recesses 155 and 156 to permit insertion within a tibial base of the present invention. FIG. 15 also illustrates an articulation insert which is used with a non-constrained femoral component to produce a non-constrained knee joint prosthesis. The advantage is that the same tibial base 40 could be used with either insert 30 or 150; thereby reducing inventory of implantable tibial components. Different types and sizes of tibial inserts could also be later surgically replaced to accommodate the needs of the patient without any need to remove and replace the implanted tibial base.

Figure 16:
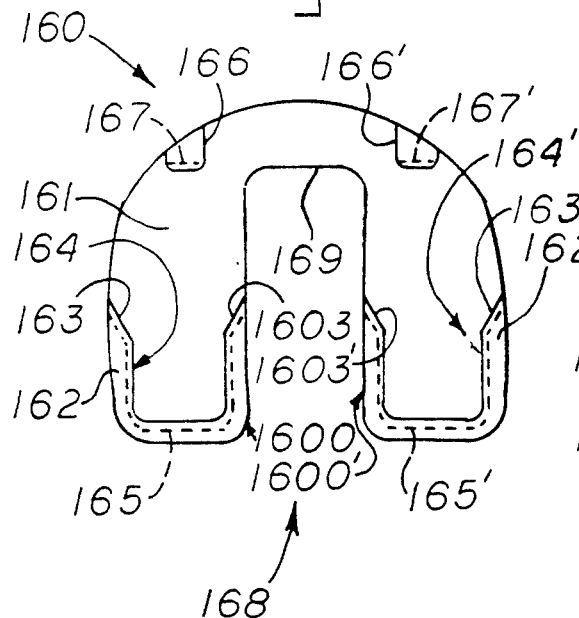
FIGS. 16-17 show base 160 and insert 170 which together form an alternative embodiment in the form of an anterior cruciate ligament-retaining tibial prosthesis.
Figure 17:
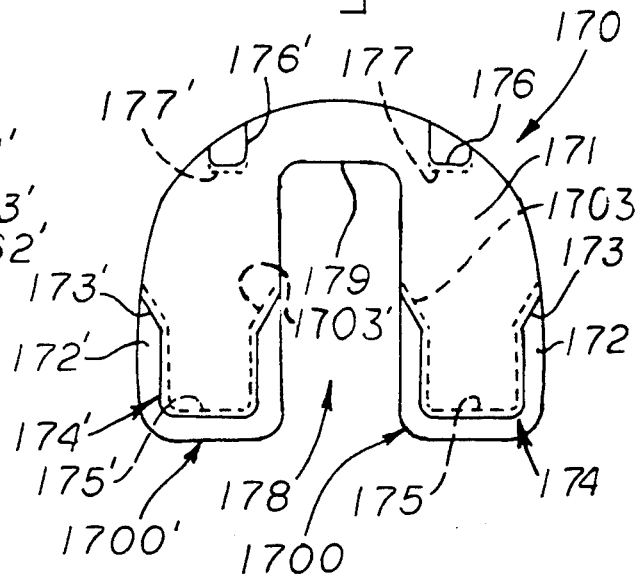

FIGS. 16 and 17 show an alternative embodiment of the present invention in the form of an anterior cruciate ligament-retaining tibial prosthesis for the right tibia composed of tibial base 160 into which articulation insert 170 is locked in place in a manner similar to that described above for the insert 30 and base 40. Deep intercondylar notch 168 in base 160 and corresponding notch 178 in insert 170 provide the necessary clearance for that ligament. Base 160 contains a substantially flat upper surface 161 (and a lower surface conventionally configured for fixation to the tibial plateau which is not shown) which is divided into a medial half 1600 and a lateral half 1600' by notch 168. Medial half 1600 has a raised wall 162 beginning at tapered area 163 which runs along the medial edge of surface 161, continues along the posterior edge of medial half 1600 and runs along notch 168 until it ends at tapered area 1603. Likewise, raised wall 162' begins at tapered area 163', runs along the lateral edge of surface 161, continues along the posterior edge of lateral half 1600' and runs along notch 168 until it ends at tapered area 1603'. Wall 162 contains a tab 164 which forms undercut 165 and wall 162' contains a tab 164' which forms undercut 165' similar to that described above for undercuts 404 and 404'.

Base 160 contains raised anterior wall 166 with undercut 167 and corresponding raised anterior wall 166' with undercut 167' where walls 166 and 166' each run along a portion of the anterior edge of surface 161, each of walls 166 and 166' being located within the central two-thirds of the anterior peripheral edge of base 160.

In view of the above discussion with respect to insert 30 and base 40, it will be readily apparent that insert 170 locks within base 160 to form a prosthesis of the present invention. The upper articulation surface of insert 170 is not shown, but is simply provided with articulation surfaces matching the configuration of the condyles of the femoral component which is to be used with this tibial component. Insert 170 with substantially flat lower surface 171 is divided into a medial half 1700 and a lateral half 1700' by notch 178 where the portions of insert 170 indicated by primed reference numerals fit within those portions of base 160 having primed reference numerals and the same applies to non-primed portions of base 160 and insert 170. When insert 170 is inserted and locked within base 160 (in the manner shown in FIGS. 2-3), edge 169 of notch 168 overlies and is even with edge 179 of notch 178.

Medial half 1700 has recess 172 with undercut 174 and lateral half 1700' has recess 172' with undercut 174' which each begin at tapered areas 173 and 173', respectively and continue along the posterior peripheral edges of each half until ending at tapered areas 1703 and 1703', respectively. Undercuts 175 and 175' correspond to the configuration of tabs 165 and 165' in base 160 so that each of recesses 172 and 172' closely mate with corresponding raised walls 162 and 162' when base 160 and insert 170 lock together. In the same fashion, insert 170 contains anterior recesses 176 with undercut 177 and 176' with undercut 177' so that after flat surface 171 is slid over raised anterior walls 166 and 166' and walls 162 and 162' mate with recesses 172 and 172', respectively, then recesses 176 and 176' mate with walls 166 and 166'.

Figure 18:
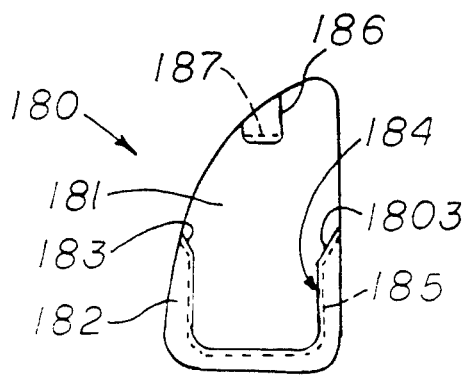
FIGS. 18-19 show base 180 and insert 190 which together form an alternative embodiment in the form of a unicondylar tibial prosthesis.
Figure 19:
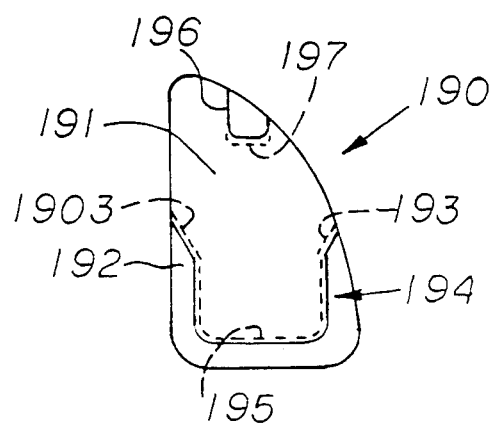

This embodiment and the one shown in FIGS. 18 and 19 show an advantage of the present invention over the central locking tab system shown in the MILLER/GALANTE Porous TIVANIUM Total Knee described above in that a centrally located locking tab does not provide enough clearance to permit such a locking mechanism to be used with the type of prostheses shown in FIGS. 16-19.

FIGS. 18-19 show a tibial base 180 and an articulation insert 190 which together form a medial unicondylar tibial prosthesis for the right femur where the upper articulation surface (not shown) of insert 190 is configured to receive one femoral condyle, rather than two, and the lower surface of base 180 (not shown) has configuration similar to that shown for the medial half of base 40 using pegs or some other means to secure base 180 to the tibial plateau. Base 180 has the same configuration as medial half 1600 of base 160 of FIG. 16 and insert 190 has the same configuration as medial half 1700 of insert 170 of FIG. 17. Insert 190 locks within base 180 in the same manner as described for FIGS. 16–17.

Thus, base 180 contains a substantially flat surface 181 containing a first raised wall 182 with tab 184 which forms undercut 185. Wall 182 starts at tapered area 183, runs along the medial, posterior and lateral edges of surface 181, and ends at tapered area 1803. Surface 181 contains a second raised wall in the form of raised wall 186 with undercut 187 located in the central portion of the anterior peripheral edge of base 180.

Insert 190 contains a substantially flat surface 191 containing a recess 192 with an undercut 194 and that recess 192 begins at tapered area 193, runs along the medial, posterior and lateral edges of surface 191, and ends at tapered area 1903. Surface 191 contains a second recess in the form of anterior recess 196 with undercut 197 located in the central portion of the anterior edge of insert 190. Recesses 192 and 196 are designed to closely mate with corresponding walls 182 and 186 to permit insert 190 to be locked within base 180 by sliding insert 190 into base 180.

Insert 170 or 190 is removed by simply raising the anterior edge of the insert above the anterior wall or walls and sliding the insert anteriorly away from the base.

To assist those skilled in the art in practicing the present invention, the following is an illustrative example of the dimensions used for the locking mechanism portions which may be used in constructing a prosthesis falling within the scope of the present invention. The rest of the configurations and dimensions are conventional. A tibial base is constructed from a cobalt-chrome alloy in the form shown for tibial base 40 having the general configuration shown in FIGS. 4–8 and an articulation insert is made from a medically acceptable prosthesis grade of ultrahigh molecular weight polyethylene in the form shown for insert 30 having the general configuration shown in FIGS. 9–14.

Referring to FIGS. 4–8, the taper (30 degrees relative to the medial/lateral edge of base 40) of each of areas 405 and 405' is such that the maximum distance between each of arrows 407 and 407' is 0.15 in. (0.381 cm) where "in."=inches and "cm"=centimeters. Area 403 of wall 41 is solid and has no undercut. In FIG. 6, the distance between surface 409 and surface 49 is 0.063 in. +0.005,−0.000 in. (0.160 cm) and the height of wall 41 above surface 49 is nominally 0.085 in. (0.216 cm). Undercut 404 (and 404') extends 0.040 in. (0.102 cm) towards the peripheral edge of base 40 and thus, undercut 404 (and 404') has dimensions of 0.063 in. by 0.040 in. (0.160 cm by 0.102 cm). In FIGS. 7–8, wall 42 (and 43) extends 0.060 in. +0.000,−0.005 in. (0.152 cm +0.000,−0.013 cm) above surface 49 and is 0.063 in. (0.160 cm) thick. Lip 70 (and 70') extends 0.010 in. +0.005,−0.0000 in. (0.025 cm +0.013,−0.0000 cm) away from inner surface 421 of wall 42.

Referring to FIGS. 9–14, the angle made by the two surfaces shown at 100 is 1 degree, 46 minutes. In FIG. 10, undercut 904 is 0.048 in. +0.000,−0.005 in. (0.122 cm, +0.000,−0.013 cm) high at tapered area 905 and is 0.063 in., +0.005, −0.000 in. (0.160 cm, +0.013, −0.000 cm) high at the point where the undercut ceases to run at an angle and that height then remains the same along the entire posterior of insert 30 until area 903 is reached. Undercut 904 extends into the plastic insert 30 a distance of 0.040 in. +0.005,−0.005 in. (0.102 cm, +0.013,−0.013 cm) along the entire length of undercut 904. Undercut 904' has the same dimensions as undercut 904. In FIG. 11, the distance between surface 909 and surface 34 is 0.085 in., +0.005,−0.000 in. (0.216 cm, +0.013,−0.000 cm). Tab 910 has the following dimensions: the distance between surfaces 911 and 912 is nominally 0.040 in. (0.102 cm); the distance between surfaces 34 and 913 is nominally 0.063 in. (0.160 cm); and the distance between surfaces 911 and 914 is nominally 0.080 in. (0.203 cm). Tab 910 is omitted in area 903.

In FIG. 12, the distance between surfaces 34 and 920 is 0.065 in., +0.000,−0.005 in. (0.165 cm, +0.000,−0.013 cm) and the distance between surfaces 921 and 922 is nominally 0.063 in. (0.160 cm). Recess 99 has a nominal height of 0.020 in. (0.051 cm) and extends 0.015 in., +0.005,−0.0000 in. (0.038 cm, +0.013,−0.0000 cm) beyond surface 922 and the center of recess 99 is nominally located 0.055 in. (0.140 cm) above surface 34.

The total tolerances are selected to provide up to 0.012 in. (0.030 cm) clearance between (a) the distance from wall 922 and wall 912 (and, likewise, between wall 922 and the lateral posterior surface corresponding to medial posterior surface wall 912) measured along a line running parallel to line 900 and (b) the directly corresponding distance between surfaces 421 and 600 and between surface 431 and 600' of base 40, both of which are measured along a line running parallel to line 400. The same tolerance is used for the distances between the medial and lateral edges of the mating surfaces measured along lines running perpendicular to line 400 and 900, respectively. This provides an insert which locks tightly, but permits insertion and removal of the insert from the base.

Other modifications of the prosthesis of the present invention will become apparent to those skilled in the art from an examination of the above patent specification and drawings. Therefore, other variations of the present invention may be made which fall within the scope of the following claims even though such variations were not specifically discussed above.

That which is claimed is:

1. A surgically implantable knee joint prosthesis for the replacement of at least one articulating surface of a proximal tibia comprising, in combination, a base having an anterior region and a posterior region corresponding to the anterior and posterior surfaces of the tibia on which it is implanted, the regions being bounded by a lateral and a medial edge, said base having a lower surface adapted to be permanently fixed to a surgically prepared superior surface of said proximal tibia and said base having an upper surface having a first retaining wall means comprising at least one undercut raised retaining wall extending along at least a portion of the peripheral edge of the posterior region of the upper surface of said base and further extending along at least a portion of the peripheral medial and lateral edges of the upper surface of said base and a second raised retaining wall means on said upper surface which is opposite and separated from the first wall means on both the lateral and the medial edge of said base, said second wall means comprising at least one raised wall extending along at least a portion of the central one-fourth to two-thirds of the peripheral edge of the anterior region of said upper surface, and a removable articulation insert of a hard synthetic polymer having an upper surface which is configured to receive at least one condyle present on a distal femur situated above said tibia and a lower surface which is adapted to closely mate with and slidingly engage said first retaining wall means and to pass over and contact said second wall means in a locking engagement such that the insert is firmly held within said base until such time as the insert is released by raising the lower surface of the insert above said second wall and sliding the insert anteriorly away from said base, said base and the insert being constructed of materials suitable for implantation within the body and having physical properties which permit such sliding and locking engagement, the separation between said first wall means and said second wall means being sufficient to permit said insert to be slidingly engaged and received in the above manner.

2. The prosthesis of claim 1 wherein said base is made of a surgically implantable metal.

3. The prosthesis of claim 1 wherein said base has a substantially flat upper surface and the insert has a substantially flat lower surface.

4. The prosthesis of claim 1 wherein said second retaining wall is recessed and the insert is adapted to receive said second recessed wall in locking engagement.

5. The prosthesis of claim 1 wherein said base and said articulation insert are sized and configured to provide a prosthesis for replacement of both lower articulating surfaces of said proximal tibia.

* * * * *